(12) United States Patent
Frei (10) Patent No.: US 10,927,338 B2
(45) Date of Patent: Feb. 23, 2021

(54) INSERT SHELF AND INCUBATOR

(71) Applicant: IKA-Werke GmbH & Co. KG, Staufen (DE)

(72) Inventor: Andreas Frei, Staufen (DE)

(73) Assignee: IKA-Werke GmbH & Co. KG, Staufen (DE)

( * ) Notice: Subject to any disclaimer, the term of this patent is extended or adjusted under 35 U.S.C. 154(b) by 82 days.

(21) Appl. No.: 15/503,527

(22) PCT Filed: Jun. 9, 2015

(86) PCT No.: PCT/EP2015/001154
§ 371 (c)(1),
(2) Date: Feb. 13, 2017

(87) PCT Pub. No.: WO2016/023603
PCT Pub. Date: Feb. 18, 2016

(65) Prior Publication Data
US 2017/0233693 A1    Aug. 17, 2017

(30) Foreign Application Priority Data
Aug. 14, 2014  (DE) ............... 10 2014 011 941.6

(51) Int. Cl.
*C12M 1/00* (2006.01)
*C12M 1/02* (2006.01)
(Continued)

(52) U.S. Cl.
CPC ......... *C12M 41/14* (2013.01); *B01F 11/0008* (2013.01); *B01F 13/08* (2013.01);
(Continued)

(58) Field of Classification Search
CPC ............... B01F 11/0008; B01F 13/08; B01F 2215/0073; C12M 27/00; C12M 27/16; C12M 41/14
See application file for complete search history.

(56) References Cited

U.S. PATENT DOCUMENTS

| 2003/0096310 A1* | 5/2003 | Hansen | B01L 3/502738 435/7.1 |
| 2004/0256963 A1* | 12/2004 | Affleck | C30B 7/00 312/209 |

(Continued)

FOREIGN PATENT DOCUMENTS

| DE | 10 2006 021852 A1 | 11/2007 |
| DE | 60 2004 006508 T2 | 1/2008 |

(Continued)

OTHER PUBLICATIONS

International Search Report from PCT application No. PCT/EP2015/001154 dated Sep. 24, 2015.

*Primary Examiner* — Gautam Prakash
*Assistant Examiner* — Lydia Edwards
(74) *Attorney, Agent, or Firm* — Budzyn IP Law, LLC (57) ABSTRACT

The insert shelf (1) is characterized in that it has at least one means (3) with which an incubation medium located in an incubation vessel placed on the insert shelf (1) can be set in motion during an incubation treatment or during an incubation process in an incubator (2). For this purpose, the at least one means (3) can be operated electrically and/or preferably moved mechanically.

21 Claims, 6 Drawing Sheets

(51) Int. Cl.
   *C12M 3/06* (2006.01)
   *B01F 11/00* (2006.01)
   *B01F 13/08* (2006.01)

(52) U.S. Cl.
   CPC ............ *C12M 27/00* (2013.01); *C12M 27/16* (2013.01); *B01F 2215/0073* (2013.01)

(56) References Cited

U.S. PATENT DOCUMENTS

2008/0056059 A1* 3/2008 Manera ............... B01F 11/0008
                                                    366/110
2010/0330663 A1* 12/2010 Baumfalk ............. C12M 27/16
                                                    435/303.3
2014/0117824 A1* 5/2014 Hayami ................... B01L 7/00
                                                    312/236

FOREIGN PATENT DOCUMENTS

| DE | 60 2004 011334 T2 | 1/2009 |
| DE | 10 2008 10780 B3 | 10/2009 |
| DE | 10 013 000044 A1 | 7/2014 |
| EP | 2 180 037 A1 | 4/2010 |
| EP | 2 489 435 A2 | 8/2012 |
| EP | 2 722 385 A2 | 4/2014 |
| WO | 2012173074 | * 12/2012 ............. C12M 1/00 |

* cited by examiner

INSERT SHELF AND INCUBATOR

The invention relates to an insert shelf that can be inserted into an incubator and used in the incubator in the use position to accommodate at least one incubation vessel.

Furthermore, the invention also relates to an incubator having a heatable incubation space and at least one replaceable insert shelf that can be inserted into the incubation space of the incubator in the use position to accommodate at least one incubation vessel containing an incubation medium.

Such insert shelves and such incubators are known from practice in various embodiments.

Thus insertion shelves for incubators are known such that these shelves, like shelves in a baking oven, can be inserted into the incubator. In their inserted use position, incubation vessels can then be placed on the insert shelves to heat the incubation media in the incubation vessels in the interior of the incubator, i.e., to subject them to an incubation treatment.

Depending on application case, it may be advantageous to also set the contents of the incubation vessels in motion during the incubation treatment. To do so, it is known that so-called shaker incubators, which are designed as agitators, for example, with an incubator hood or as incubators that can be placed on a shaker table, can be used for this purpose.

In the case of incubators placed on a shaker table in particular, it may be a disadvantage that, with this approach, the entire incubator must be moved in order to set the incubation vessel, which is relatively small and lightweight in relation to the incubator, together with its contents in motion. To move the incubation medium in the desired manner, with these shaker incubators known in the past, an unnecessarily large mass must also be moved, but this may be associated with a high power demand accordingly.

The object of the invention is therefore to create an insert shelf of the type defined in the introduction and an incubator as defined in the introduction, which will allow more efficient shaking of the incubation media during an incubation treatment.

With the insert shelf defined in the introduction, this object is achieved by the features of patent claim 1. This object is achieved in particular by the fact that the insert shelf defined in the introduction is provided with at least one means with which an incubation medium, which is inside the incubation vessel placed on the insert shelf in the use position, can be set in motion.

The incubation medium in the at least one incubation vessel can be set in motion in this way with the help of the insert shelf without having to agitate the entire incubator. Furthermore, it is thus possible to retrofit existing incubators or even incubators designed as a heating cabinet with such an insert shelf and thereby expand the scope of functions of existing incubators.

It may be expedient in particular if the at least one means can be operated electrically. Alternatively or additionally, the at least one means may also be set in motion mechanically, and an incubation vessel placed on the insert shelf in the use position and an incubation medium inside the incubation vessel can also be set in motion in the desired manner at least indirectly due to the mechanical movement induced by said means.

In a preferred embodiment of the invention, it is possible to provide that the at least one means of the insert shelf can be moved mechanically with respect to a frame that is stationary in the use position or an insert frame of the insert shelf. It is thus possible for the insert shelf to be inserted into an incubator by means of its stationary frame or insert frame and it can be stationary relative to the incubator itself while the at least one means can be moved mechanically relative to the stationary frame or the insert frame and thus relative to the incubator in order to set the incubation medium in motion as desired in the at least one incubation vessel placed on the insert plate.

In one embodiment of the insert shelf according to the invention, it is possible to provide that the insert shelf is designed as at least one means for moving the incubation medium and has a setup area that is movable in at least one direction of movement for holding at least one incubation vessel and a frame that is stationary with respect to the movable setup area, for example, the insert frame mentioned above, with which the insert shelf can be secured in its use position, after having been inserted into the incubator.

The insert shelf may have a drive device with which the movable setup area of the insert shelf is at least indirectly movable. In addition or as an alternative to this, the insert shelf may have a drive device with which the incubation medium in the incubation vessel placed on the insert shelf can be set in motion at least indirectly.

It may be expedient if the insert shelf and/or a setup area of the insert shelf already mentioned above, for example, has at least one magnetic stirring drive as a means for setting in motion the incubation medium, with which a rotating magnetic field can be generated for driving at least one magnetic stirrer that can be inserted into an incubation vessel.

This at least one magnetic stirring drive can be driven by means of a drive device of the insert shelf as already mentioned above, for example.

With this embodiment of the invention as described above, it is particularly advantageous that the insert shelf need not be moved but instead may remain stationary because the incubation medium can be moved with the help of the magnetic stirrer which is driven by the magnetic stirring drive, which is similar to that of a commercial magnetic stirrer.

However, it should also be pointed out that a mechanically movable setup area with at least one magnetic stirring drive can be combined in or on the insert shelf or the setup area of the insert shelf and can lead to particularly good results.

In a particularly advantageous embodiment of the invention, the at least one magnetic stirring drive may have a rotatably mounted carrier disk with at least one, preferably two or more magnets disposed on the carrier disk and/or permanent magnets wherein the carrier disk can be driven mechanically and can be set in rotation by means of a drive device of the insert shelf such as the one already described above, for example, in order to generate a rotating magnetic field with which a magnetic stirrer can be set in motion.

In the case of a mechanically driven magnetic stirring drive with at least one magnet and/or permanent magnet, it may be possible advantageously to omit the magnetic coils, which generate waste heat during operation which can make accurate temperature control of an incubation process difficult.

It may be expedient if the at least one magnetic stirring drive is disposed beneath a setup area of the insert shelf for at least one incubation vessel at a stirring location in the use position.

For the simultaneous incubation treatment and movement of multiple incubation vessels, it may be advantageous if the insert shelf and/or a setup area of the insert shelf already mentioned above, for example, has a plurality of magnetic storing drives distributed preferably uniformly for driving a plurality of magnetic stirrers that can be used in incubation vessels. These multiple magnetic stirring drives can then preferably be disposed each in one stirring location, preferably beneath one/the setup area of the insert shelf.

It should be pointed out here that, in one embodiment of the insert shelf according to the invention, it is possible to provide for this plurality of preferably uniformly distributed magnetic stirring drives to be controllable/regulable independently of one another in order to be able to set the incubation media to different extents in the individual incubation vessels.

It may be expedient if the setup area is disposed on a vibrating frame, which can be set in motion by means of one/the drive apparatus, in particular in its use position on its upper side, wherein the vibrating frame is supported so that it is movable relative to the frame of the insert shelf. Thus the movable setup area can be moved with the help of the movable vibrating frame in a particularly simple manner in comparison with the stationary frame of the insert shelf, which is stationary relative to the incubator in the use position.

It may be advantageous if the vibrating frame has a greater thickness or height than the frame and/or is disposed in such a way that it protrudes upward beyond the frame of the insert shelf when in the use position. In this way it is possible for a setup area which is provided on the top side of the vibrating frame not to collide with the stationary frame of the insert shelf surrounding the vibrating frame during the movement of the vibrating frame and during the movement of the setup area. In addition or as an alternative to that, the setup area which is movable relative to the frame may be disposed in a plane at a distance from the surface of the frame, in particular parallel to it. It is possible in this way to ensure that the setup area does not collide with the stationary frame during its movement relative thereto and that it can even be brought into a position overlapping with the stationary frame of the insert shelf at least temporarily.

This may be advantageous in particular when the setup area is to be set in motion with different amplitudes of movement in order to set in motion the incubation medium in the at least one incubation vessel.

In one embodiment of the insert shelf according to the invention, which is especially important, it is possible to provide that the insert shelf, in particular the drive apparatus of the insert shelf has a drive motor which is preferably designed as an electric motor. The drive motor may be connected to the setup area and/or to the vibrating frame at least indirectly, preferably by way of the drive apparatus, in order to set in motion the setup area and thereby the incubation medium. This creates an insert shelf with which even existing incubators or incubation cabinets can be retrofitted and thus can be equipped with an additional function, namely the possibility of agitation of incubation media during the incubation process or the incubation treatment.

It may be expedient if the insert shelf, in particular a drive device of the insert shelf, for example, the one described above, has a belt drive, which connects the vibrating frame and/or the setup area of the insert shelf and/or the at least one magnetic stirring drive to a drive motor, for example, the one described above at least indirectly and by means of which a drive torque of the drive motor can be transferred to the setup area which is movable relative to the frame of the insert shelf and/or to the vibrating frame and/or to the at least one magnetic stirring drive. In this way, the drive motor can be set up in a suitable location even at a certain distance from the setup area and/or the vibrating frame and/or the at least one magnetic stirring device and this distance between the drive motor and the vibrating frame or the movable setup area can be bridged with the help of the belt drive.

For transfer of torque, on the one hand, and desired movement patterns, on the other hand, it may be expedient if the insert shelf, the drive apparatus of the insert shelf has a drive disk connected, for example, to the drive motor already mentioned above in particular for moving the setup area and/or the vibrating frame. This drive disk is mounted so that it is connected to the setup area and/or the vibrating frame and is rotatable relative to the stationary frame of the insert shelf. The drive disk may preferably be connected to the drive motor by means of a drive belt of the insert shelf, for example, the one already mentioned above. The output disk may have an eccentric design and/or an eccentric journal disposed eccentrically on the output disk. This eccentric journal may be connected to the setup area at least indirectly and may serve to convert a rotational movement of the output disk into an eccentric movement of the vibrating frame and/or the setup area of the insert shelf. Depending on the eccentricity of the output disk and/or the arrangement of the eccentric journal, the desired movement pattern, for example, a circular vibration or a rotation can be transferred to the at least one incubation vessel set up on the insert shelf.

In order for the insert shelf to enable a uniform heat distribution inside the incubator into which it is inserted in the use position, it may be expedient if the frame of the insert shelf includes the setup area and/or the vibrating frame of the insert shelf at a distance in at least some areas and/or if the insert shelf has at least one, preferably a plurality of convection openings, in particular disposed uniformly on the insert shelf and passing through the insert shelf. It is possible in this way for air warmed/heated by the incubator to be able to flow through the clearance between the frame of the insert shelf and the setup area and/or the vibrating frame and thus permit a uniform heat distribution in an interior space of the incubator. The same thing is also true of an insert shelf having at least one convection opening passing through the insert shelf by means of which it is then possible to achieve an exchange of and a uniform distribution of hot air.

If the insert shelf has at least one handle and/or at least one carrying handle on the side facing an insert opening of the incubator when in the use position of the insert shelf then the insert shelf can be transported in a particularly simple manner, on the one hand, while being easily inserted into and taken out of its use position in the incubator and/or pulled out or inserted and removed, on the other hand.

It may also be expedient if the insert shelf has at least one clamping handle with which the insert shelf can be secured in its use position, after being inserted and/or pushed into the incubator. This clamping handle may be connected to a clamping mechanism, which is provided on the insert shelf, for the operation of which the clamping handle can be moved from an open position into a clamping position. Then the insert shelf can be secured in its use position in and/or on the incubator by means of this clamping mechanism.

To also be able to use the insert shelf with existing incubators or incubation cabinets, it may be expedient if the insert shelf is designed as an insert shelf and can be inserted into an incubator, in particular into holding elements in an incubator designed as holding rails. To be able to secure the insert shelf in its use position in the incubator and thereby prevent any relative movement between the insert shelf and the incubator, it may be advantageous if the insert shelf has at least one centering element, in particular at least one centering journal and/or at least one centering hole, wherein the at least one centering element of the insert shelf can then cooperate with a correspondingly designed centering element of the incubator to bring the insert shelf into a predetermined position, which is defined by the centering elements, and to hold it there.

The at least one centering element of the insert shelf may be designed on an insert opening of the incubator in the use position on a side of the insert shelf, facing away from an insert opening of the incubator, i.e., on its rear side, for example.

To be able to reliably transfer a movement of the insert shelf, in particular its setup area, to the at least one incubation vessel setup in use position on the insert shelf, it may be expedient if the insert shelf and/or the setup area of the insert shelf has at least one holding element for the at least one incubation vessel. The at least one holding element may be, for example, a nubby mat and/or an incubation vessel holder which serves to secure at least one incubation vessel on the setup area.

Furthermore, it is possible for the insert shelf and/or the setup area of the insert shelf to be provided with a slip-preventing coating. This may be provided additionally or alternatively.

It should be pointed out that a movement of the movable setup area and/or of the vibrating frame of the insert shelf and/or a movement that can be transferred to the incubation vessel by means of the insert shelf may be a tumbling movement and/or a tilting movement and/or a rotational movement and/or an agitating movement and/or a stirring movement. Whereas the stirring movement is expediently induced by means of a magnetic stirring drive and a stirring magnet that is magnetically coupled to the magnetic stirring drive, a tumbling movement and/or the tilting movement and/or a rotational movement and/or an agitating movement can be implemented particularly well by means of the vibrating frame and in particular with the help of the output disk described above.

The object described above is achieved with the incubator defined in the introduction through the features of patent claim 17. In particular this object is achieved by the fact that the at least one insert shelf of the incubator is an insert shelf according to any one of claims 1 to 16.

It may be expedient if the incubator has a drive motor that can be connected to a drive apparatus, for example, of the type already described above, of the at least one insert shelf. This drive motor may preferably be designed as an electric motor. With this drive motor, a movable setup area, for example, of the type already described above, of the at least one insert shelf that is inserted and/or placed into the incubator in the use position can be set in motion. However, it is also possible to drive a magnetic stirrer drive, for example, the one already described above, of the insert shelf by means of this drive motor.

The incubator, in particular the incubation space of the incubator and/or a housing of the incubator, may expediently have an opening, preferably designed as an insert opening, for inserting or positioning the at least one insert shelf, wherein the opening can preferably be closed by means of a cover and/or a door.

To be able to arrange at least one insert shelf in various positions in the interior of the incubation space of the incubator or to arrange multiple insert shelves in the incubator at the same time, it may be expedient if the incubator, in particular in its incubation space, has a plurality of holding elements, preferably disposed so they are spaced a distance apart from one another vertically in the use position, for the at least one insert shelf by means of which [holding elements] the at least one or a plurality of insert shelves can be disposed at different holding stages in the incubation space, preferably disposed one above the other.

The holding elements disposed at a distance from one another vertically may designed, for example, as holding rails, like those of a baking oven and/or holding eyes, the at least one insert shelf of which can be held in a form-fitting manner in the use position. It should be pointed out that the use of holding rails is preferred because in this way the at least one insert shelf can be inserted into its use position in the interior of the incubator in a particularly simple manner.

To be able to reliably specify the at least one insert shelf or the plurality of insert shelves in their use positions in the incubator, it may be expedient if, on an inside wall of its incubation space in particular, the incubator has at least one centering element, which is disposed and designed to fit the at least one centering element of the insert shelf. This centering element of the incubator is then of course designed to correspond to the centering element of the insert shelf. This means that, when the centering element of the insert shelf is designed as a centering journal, the centering element of the insert shelf is designed as a centering hole or a centering opening. If the centering element of the insert shelf is designed as a centering hole, then the centering element of the incubator is designed as a centering journal that fits in the centering hole corresponding to that.

It may be advantageous if the incubator, in particular the incubation space and/or an inside wall of the incubator has/have at least one centering element designed to correspond to the centering element of the insert shelf in each of the holding stages for the at least one insert shelf spaced a distance apart from one another vertically in the use position. It is thus possible to position the at least one insert shelf or multiple insert shelves securely in different holding stages in the incubator.

It may be expedient if the drive motor that can be coupled to the drive device of the at least one insert shelf is disposed on the incubator, in particular on a housing of the incubator. A drive torque of the drive motor can be transferred to the at least one insert shelf, in particular to the movable setup area and/or to the vibrating frame of the insert shelf, preferably by means of a drive belt, for example, as already mentioned above, of the insert shelf. In this embodiment of the incubator, it is especially advantageous and therefore worth mentioning that the insert shelf here need not have a drive motor itself and therefore can be cleaned better, for example, which is often necessary in the case of processing biological samples. Furthermore, it is possible in this way to obviate the need to take into account the release of heat that occurs due to operation of the drive motor in the temperature control of the incubator, because the drive motor here is set up outside of the incubation space on the housing of the incubator.

To transfer the torque from a drive motor of the incubator, already mentioned above, for example, to the at least one insert shelf, it may be advantageous if the at least one insert shelf has a PTO shaft, and if the incubator for the PTO shaft has a suitably disposed and designed coupling point such that an output shaft of the drive motor can be coupled to the PTO shaft of the at least one insert shelf at the coupling point of the incubator. In this way, the torque of the drive motor of the incubator can be transferred to the movable setup area and/or to the vibrating frame and/or to the at least one magnet stirring drive of the at least one insert shelf. The PTO shaft of the insert shelf may be disposed in particular on a side or rear side of the insert shelf, which is used in the incubation space in the use position.

To be able to drive at least one insert shelf into several of the different holding stages, it may be expedient if the incubator has a plurality of coupling points positioned so they fit with the holding stages for a PTO shaft of the at least one insert shelf. The incubator may preferably have a number of coupling points positioned so that they fit with the holding stages, such that the number corresponds to the number of holding stages to be able to operate the at least one insert shelf by means of its PTO shaft in each of the holding stages present on the incubator.

However, it is also possible for the drive motor to be disposed in a plurality, preferably in a number of positions that fit with the holding stages and correspond to the number of holding stages can be disposed on the incubator and/or on a housing of the incubator. In this way the drive motor can always be brought into the proper position on the incubator, which fits with the holding stage, into which the insert shelf is pushed or inserted into the incubator.

However, it is also possible for the incubator to have a plurality of drive motors, in particular a number of drive motors disposed so they fit the holding stages corresponding to the number of holding stages. A drive motor for a suitably equipped insert shelf may be present on each of the different holding stages in this way. Furthermore, it is also possible in this way to provide an incubator in which incubation vessels and/or the incubation media in these vessels positioned on different insert shelves to be movable simultaneously but independently of one another, whether with different movement patterns and/or different movement amplitudes, or with different movement frequencies and/or movement intensities.

It should be pointed out that in the case of an insert shelf having a drive motor, this drive motor may be connected to an external power source for the drive motor. However, it is also possible for the insert shelf, in particular when it has its own drive motor, to have a battery and/or a rechargeable battery as a current source for the drive motor.

Exemplary embodiments of insert shelves according to the invention and an incubator according to the invention are described in greater detail below on the basis of the drawings, in which in sometimes highly schematized diagrams.

In the following description of various embodiments of the invention, elements that have the same or similar function are also labeled with the same reference numerals even if the design or shaping are different.

Figure 1:
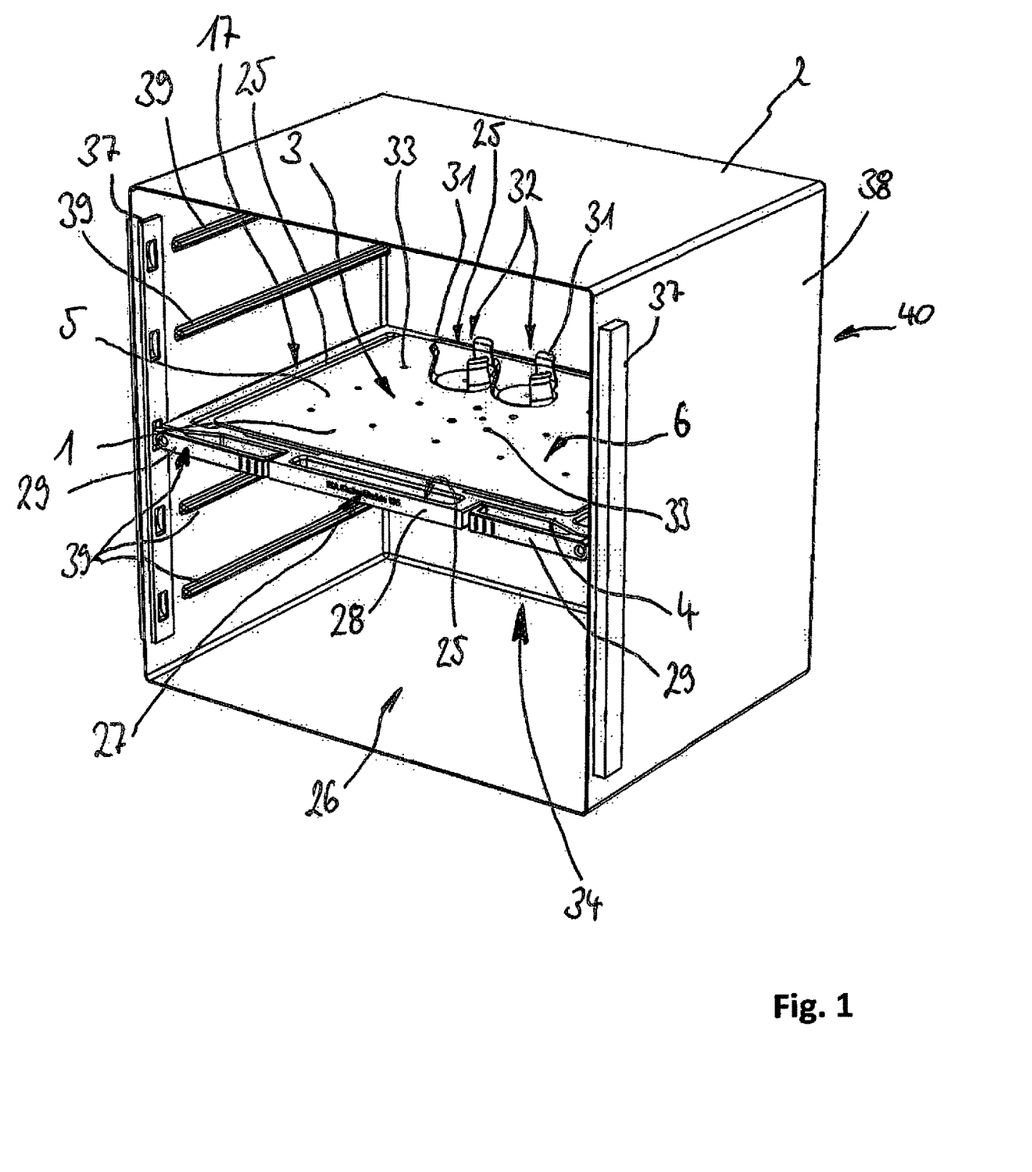
FIG. 1 shows a perspective side view of an incubator according to the invention shown in a greatly schematized diagram, with an insert shelf according to the invention inserted into an incubation space of the incubator with two incubation vessel holders discernible on the insert shelf.
Figure 2:
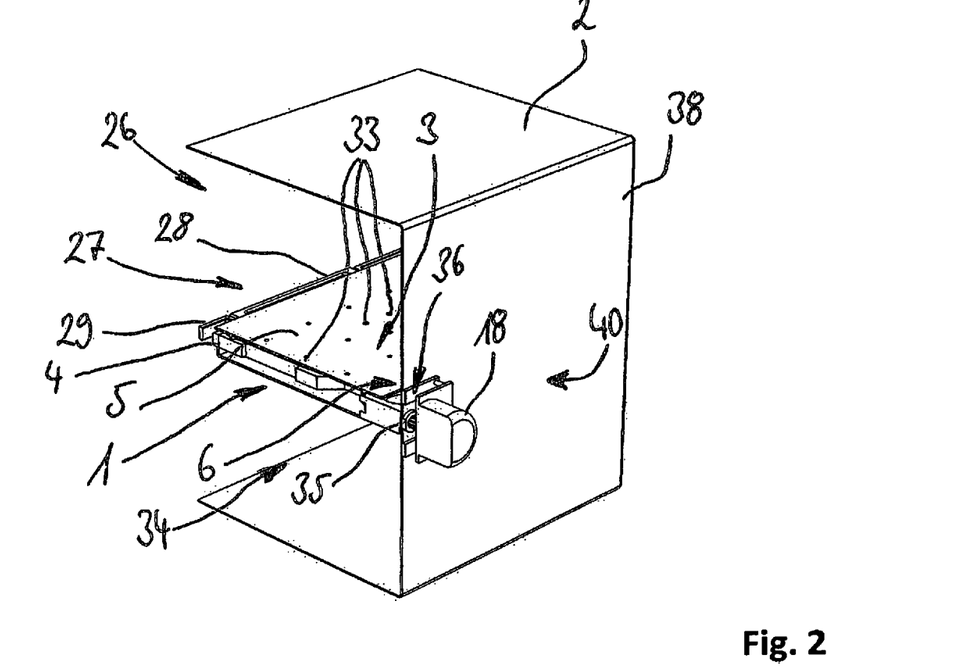
FIG. 2 shows a perspective side view of the incubator illustrated in FIG. 1, wherein a side wall of the incubator is not shown for the sake of a simpler diagram, so that the view into the interior of the incubator is free and a drive motor which is shown in sectional view on the rear side of the incubator can be coupled to the insert shelf, which is in the use position, by means of a PTO shaft.

FIGS. 1 and 2 as well as 4 through 11 each show an insert shelf, which is labeled on the whole as 1 and can be positioned in an incubator 2 in the use position, in particular being inserted into it.

The insert shelf 1 serves to receive at least one incubation vessel (not shown in the figures), in which there is an incubation medium to be incubated. All of the insert shelves 1 illustrated in the figures are provided with at least one means 3, with which an incubation medium, which is inside the at least one incubation vessel placed on the insert shelf 1 can be set in motion.

The at least one means 3 can be driven electrically and can be moved mechanically with respect to a stationary frame or insert frame 4 of the insert shelf 1, the frame being stationary in the use position. The insert shelf 1 illustrated in FIGS. 4 through 9 has a setup area 5, which can be set in motion in at least one direction of movement as the at least one means 3 for movement of the incubation medium, to receive at least one incubation vessel and one frame 4, which is stationary with respect to the movable setup area 5, with which the insert shelf 1 can be secured in its use position inserted into the incubator 2.

This frame 4 is designed as an insert frame with which the insert shelf 1 can be inserted into the incubator 2.

The insert shelf 1 has a drive apparatus 6 with which the movable setup area 5 of the insert shelf 1 is movable at least indirectly and with which the incubation medium which is in an incubation vessel placed on the insert shelf 1 can be set in motion at least indirectly.

Figure 10:
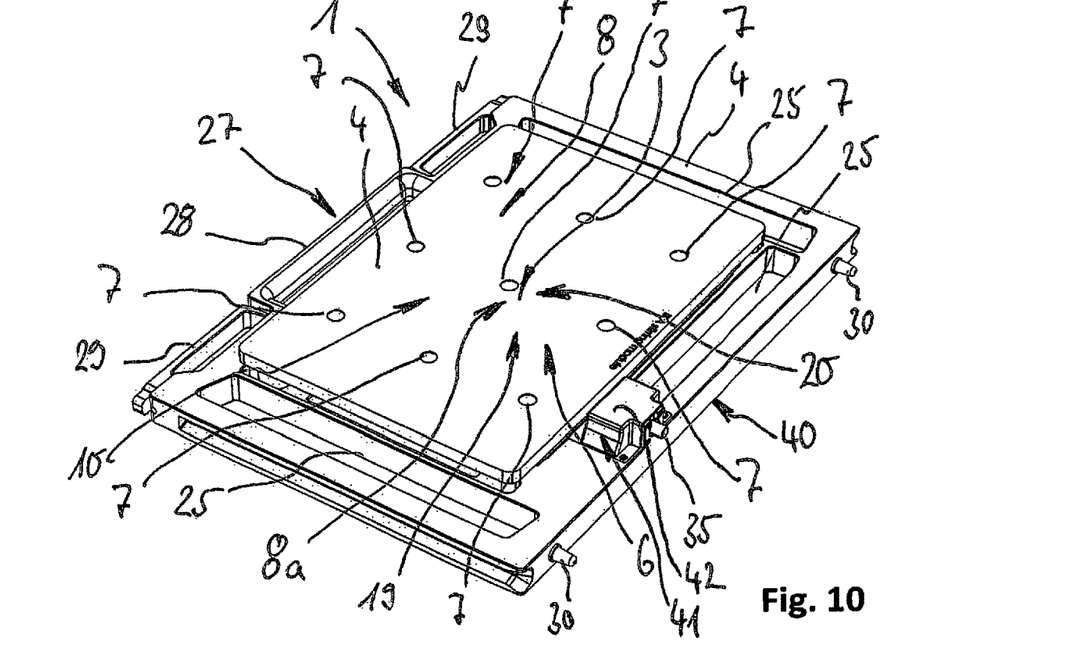
FIG. 10 shows a perspective top view of another insert shelf according to the invention, which has a plurality of magnetic stirring drives that cover the setup area, as well as FIG. 11 shows a perspective view of the insert shelf according to the invention as illustrated in FIG. 10, with the setup area removed, showing a total of nine magnetic stirring drives, each having two magnets, connected to one another by a belt drive; the magnetic stirring drives can be driven by means of a PTO shaft disposed on the rear side of the insert shelf and a belt drive.
Figure 11:
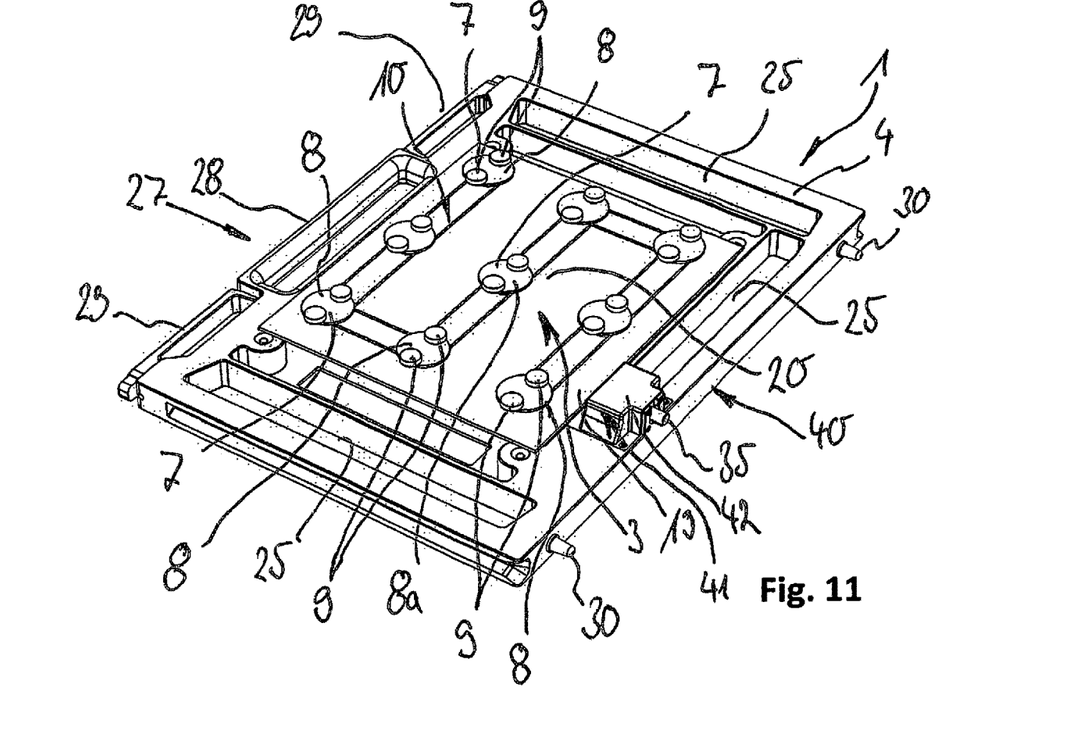

The insert shelf 1 shown in FIGS. 10 and 11 has a total of nine magnetic stirring drives 7 as the means 3 for inducing movement of the induction medium, these drives being equipped so that each generates a rotating magnetic field to drive a magnetic stirrer that can be inserted into the incubation vessel.

FIG. 11 also shows the design of the magnetic stirring drives 7 that are used.

Each of the magnetic stirring drives 7 has a rotatably mounted carrier disk 8 on which two magnets or permanent magnets 9 that are disposed on the top side and offset by 180° from one another in the use position are provided. The carrier disks 8 of the magnetic stirring drives 7 are interconnected, as shown in FIG. 11, by means of a common drive belt 10. It is thus possible that only one carrier disk 8a of the carrier disks 8 of the total of nine magnetic stirring drives 7 must be driven because the torque transferred from the drive apparatus 6 to the one carrier disk 8a can be transferred by means of the drive belt 10 to the other carrier disks 8 which are connected to one another by the drive belt 10. In the exemplary embodiment of the insert shelf 1 shown in FIGS. 10 and 11, the middle carrier disk, labeled with reference numeral 8a, is the one that can be driven by the drive apparatus 6 of the insert shelf.

The insert shelf 1 shown in FIGS. 10 and 11 has a plurality of uniformly distributed magnetic stirring drives 7 disposed beneath its setup area 5, so that they are uniformly distributed for driving a plurality of magnetic stirrers that can be used in incubation vessels.

With the insert shelves 1 illustrated in FIGS. 1 and 2 as well as 4 through 9, the setup area 5 in the use position is disposed on the top side of the movable vibrating frame 11 that can be set in motion by means of the drive device 6, wherein the vibrating frame 11 is mounted so that it can be moved relative to the stationary frame 4 of the insert shelf 1.

Figure 7:
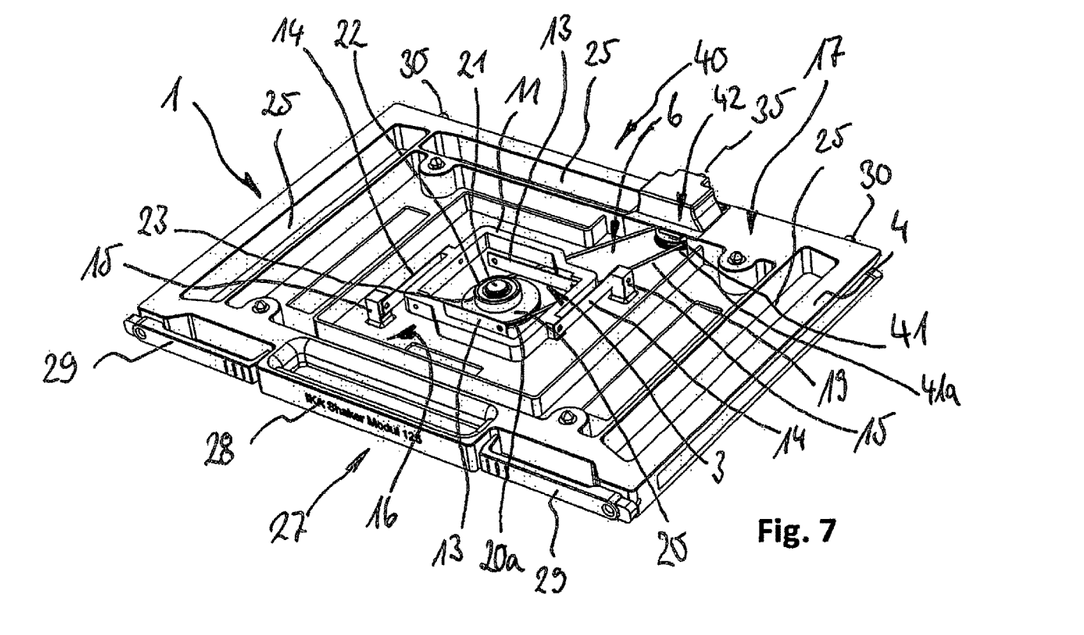
FIG. 7 shows a perspective top view of the insert shaft illustrated in FIG. 6, wherein the setup area of the insert shaft has been removed and a vibrating frame as well as an output disk and the belt drive of the insert shelf can be seen.

The vibrating frame 11 is constructed in multiple parts and has a flange element 12 on which the setup area 5 of the insert shelf 1 is fastened in the use position. The flange element 12 is shown in sectional view in FIG. 8. In FIG. 7, where the vibrating frame 11 can be seen particularly well, this flange element 12 is omitted for the sake of a better overview. The flange element 12 is mounted to be movable by means of an internal pair of vibrating springs 13 with respect to the actual vibrating frame 11. The vibrating frame 11 and the flange element 12 are again mounted movably about a second pair of outer vibrating springs 14 with respect to the insert shelf 1 and its stationary frame 4. The vibrating frame 11 is suspended by means of its second pair of vibrating springs 14 on two fastening heads 15, which are disposed on a base plate 16 of the insert shelf in the use position so that they protrude upward.

The vibrating frame 11 is disposed in such a way that it protrudes upward beyond the frame 4 in the use position, so that the setup area 5, which is movable relative to the frame 4, is disposed in a plane that is parallel to the surface 17 of the frame 4 and at a distance from it.

Figure 9:
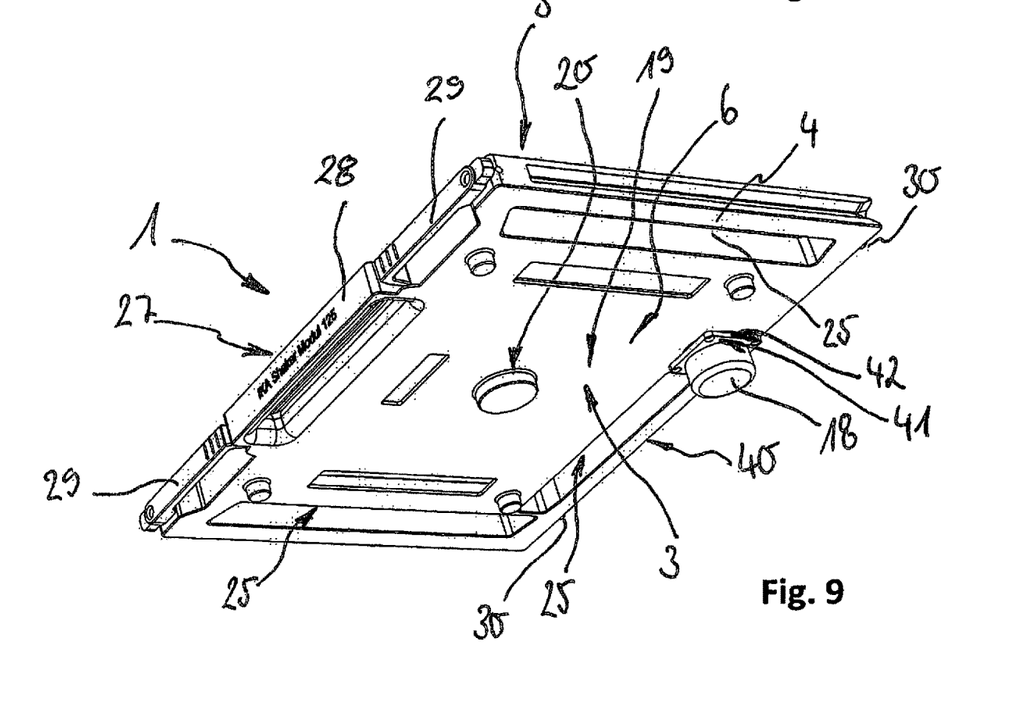
FIG. 9 shows a perspective bottom view of another insert shelf according to the invention, wherein a drive motor for the mechanically movable setup area of the insert shelf can be seen on the bottom side of the insert shelf.

In the exemplary embodiment of the insert shelf 1 illustrated in FIG. 9, the insert shelf 1 has a drive motor 18 designed as an electric motor, which is connected at least indirectly to the setup area 5 by means of the drive apparatus 6 and is thus also connected indirectly to the vibrating frame 11 in order to set in motion the setup area 5 and therefore the incubation medium in the at least one incubation vessel positioned in the setup area 5 in the use position.

Figure 5:
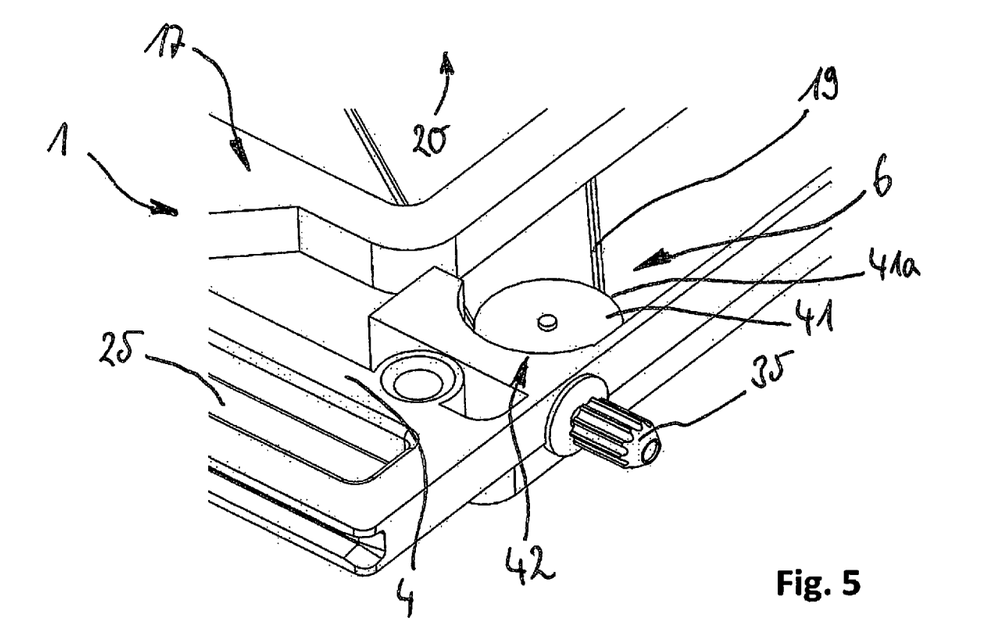
FIG. 5 shows a detailed diagram of the insert shelf illustrated in FIGS. 1, 2 and 4 in which the PTO shaft and a drive belt of the insert shelf can be seen.
Figure 6:
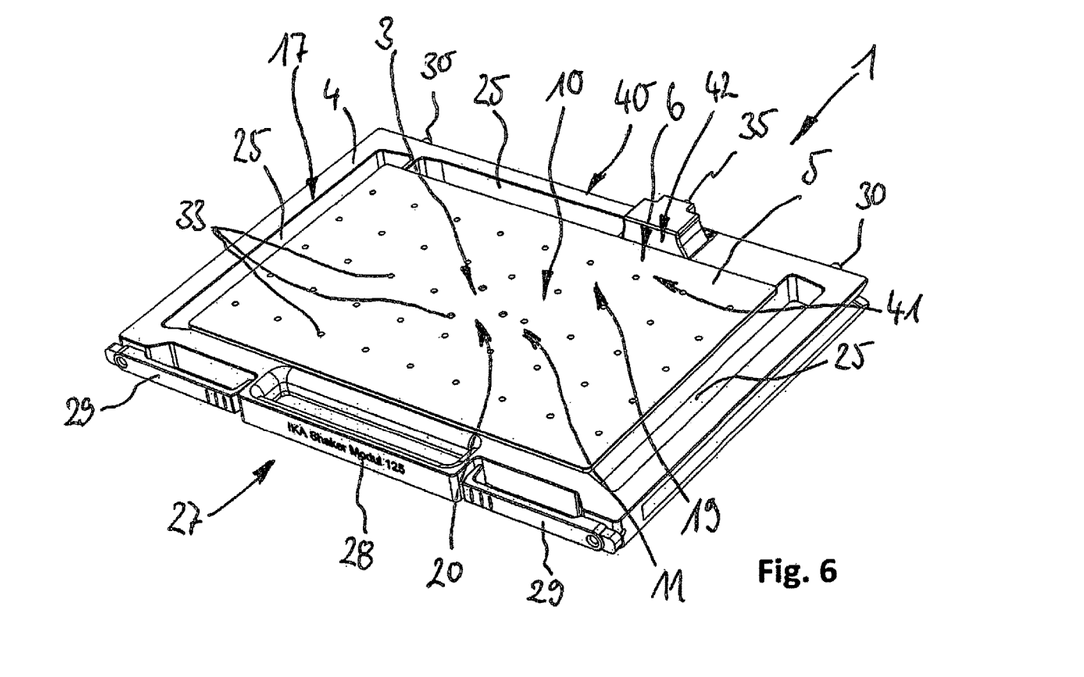
FIG. 6 shows a perspective view of another insert shelf according to the invention having a PTO shaft on its rear side as well as having three convection openings surrounding the setup area of the insert shaft and having two centering journals disposed on the rear side of the insert shaft.
Figure 8:
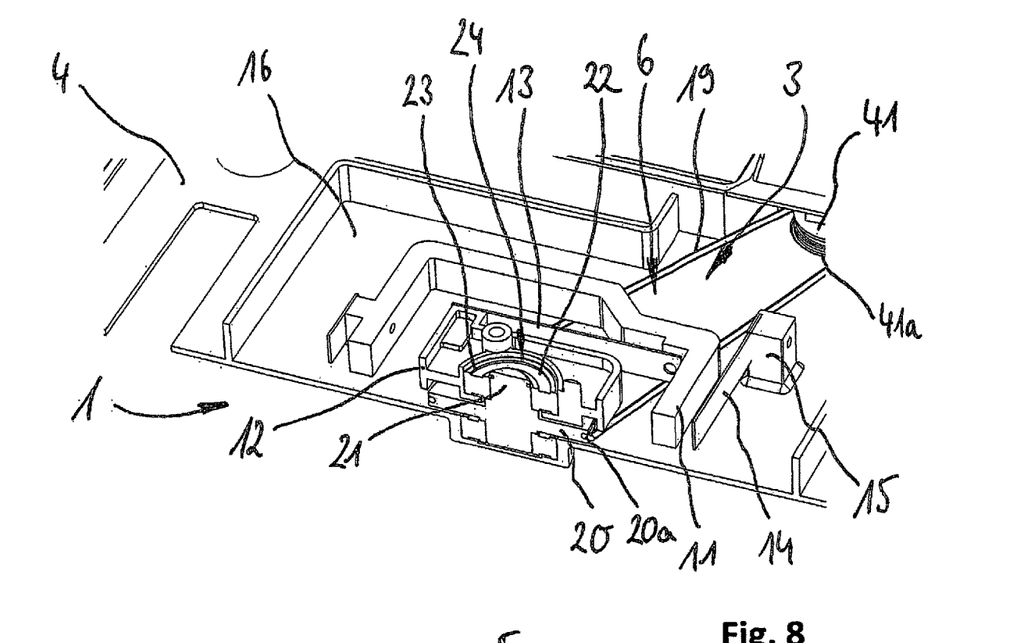
FIG. 8 shows a perspective sectional view of an insert shelf according to the invention in which the vibrating frame, an output disk with eccentric journals and a flange element can be seen, wherein the eccentric journal is shown in its use position in the flange element for transfer of its movement to the setup area of insert shelf (not shown)

FIGS. 5, 7 and 8 shows that the insert shelf 1 has a belt drive 19, which connects the vibrating frame 11 and thus the setup area 5 of the insert shelf 1 to the drive motor 18 at least indirectly, and by means of which a drive torque of the drive motor 18 can be transferred to the setup area 5, which is movable relative to the frame 4 of the insert shelf 1 and to the vibrating frame 11.

In the exemplary embodiment of the insert shelf 1 with the magnetic stirring drives 7 according to FIGS. 10 and 11, the belt drive 19 serves to transfer the drive torque of the drive motor 18 to the carrier disk 8a of the nine carrier disks 8.

The insert shelf 1, in particular the drive apparatus 6 of the insert shelf 1 for moving the setup area 5 and/or the vibrating frame 11 has an output disk 20 which is connected via the belt drive 19 to the drive motor 18 and is connected to the setup area 5 and to the vibrating frame 11 and is mounted, so that it is rotatable relative to the stationary frame 4 of the insert shelf 1. On its circumference the output disk 20 is provided with a groove 20a for the belt drive 19 in which the belt drive 19 is held securely.

The belt drive 19 runs between the output disk 20, which was already mentioned above and an input disk 41, which is in turn connected to a gear step 42, by means of which the torque of the drive motor 18 can be transferred to the input disk 41, the belt drive 19 and finally to the output disk 20 and the elements downstream from the output disk 20. The input disk 41 also has a corresponding groove 41a for receiving the belt drive 19.

On its top side the output disk 20 has an eccentric journal 21 whose longitudinal central axis runs parallel to an axis of rotation of the output disk. According to FIG. 8 an eccentric bearing 22 whose outer bearing ring 23 engages in a bearing receptacle 24 of the flange element 12 in the use position is placed on the eccentric journal 21. In this way the rotational movement of the output disk 20 can be converted into an eccentric orbital movement of the eccentric journal 21 and thus also into an eccentric orbital movement of the bearing ring 23 of the eccentric bearing 22 and finally also the setup area 5 of the insert shelf 1 mounted on the flange element 12.

In the case of the insert shelf 1 shown in FIGS. 10 and 11 with the total of nine uniformly distributed magnetic stirring drives 7, it should be pointed out that the driven carrier disk 8a here is connected to the output disk 20 in a rotationally fixed manner in order to transfer the torque from the drive motor 18 also to the eight other magnetic stirring drives 7 with the help of the drive belt 10 which connects the magnetic stirring drive 7 to one another. The rotationally fixed connection between the carrier disk 8a and the output disk 20 is not shown in the figures.

The insert shelves 1 illustrated in the figures have a total of three or four convection openings 25, which are disposed so that they are distributed uniformly on the insert shelf 1 and pass through the insert shelf 1, depending on the exemplary embodiment, and through which air heated by the incubator 2 can flow from an area beneath the insert shelf 1 into an area above the insert shelf 1 and vice versa. Convection openings 25 can facilitate an accurate precise temperature management of the incubation processes even when the insert shelf 1 is inserted into the incubator 2.

These figures show that the insert shelf 1 has a handle area in the form of a carrying handle 28 on a side 27 facing an insert opening 26 in the incubator 2 in the use position of the insert shelf 1. The carrying handle 28 is also flanked by a total of two clamping handles 29 by means of which the insert shelf 1 can be secured in its use position inserted into the incubator 2 in that the clamping handles 29 cooperate with a clamping strip 37 on the incubator 2 in the clamping position.

The insert shelves 1 illustrated in the figures are designed as insert shelves and can be inserted into the incubator 2 as holding elements of the incubator 2 designed as holding rails 39.

Each of the insert shelves 1 illustrated in the figures has a total of two centering elements designed as centering journals 30 on a side 40 facing away from the insert opening 26 of the incubator 2 in the use position of the insert shelf 1, these centering elements engaging in a centering element, namely here a centering hole formed on the incubator 2 in the use position.

According to FIG. 1, the insert shelf 1 has a total of two holding elements 31 illustrated here only as an example, on the top side of its setup area 5, these holding elements being designed as incubation vessel holders 32 in the exemplary embodiment illustrated in FIG. 1. These holding elements 31 which are designed as incubation vessel holders 32 can be inserted into fastening holes 33 disposed so that they are distributed uniformly on the top side of the setup area 5 so that on the one hand a plurality of holding elements 31 can be disposed on the setup area 5 and on the other hand a formation of the holding elements 31 on the top side of the setup area 5 can be selected freely within limits.

The figures do not show that the setup area 5 of the insert shelf 1 may also be provided with a non-slip coating and/or with a nubby mat as a non-slip layer to secure at least one incubation vessel on the setup area 5.

A rotational movement is the movement executed by the movable setup area 5 and the vibrating frame 11 of the insert shelf 1 and thus it is a movement that can be transferred to the incubation medium.

Figure 3:
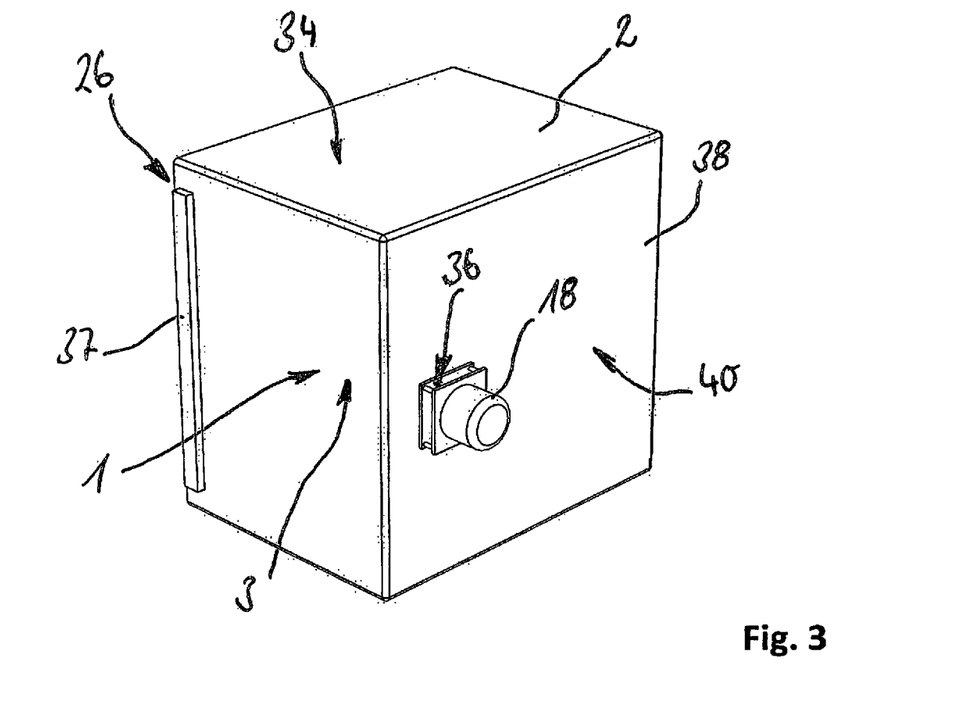
FIG. 3 shows a perspective rear view of the incubator illustrated in FIGS. 1 and 2.
Figure 4:
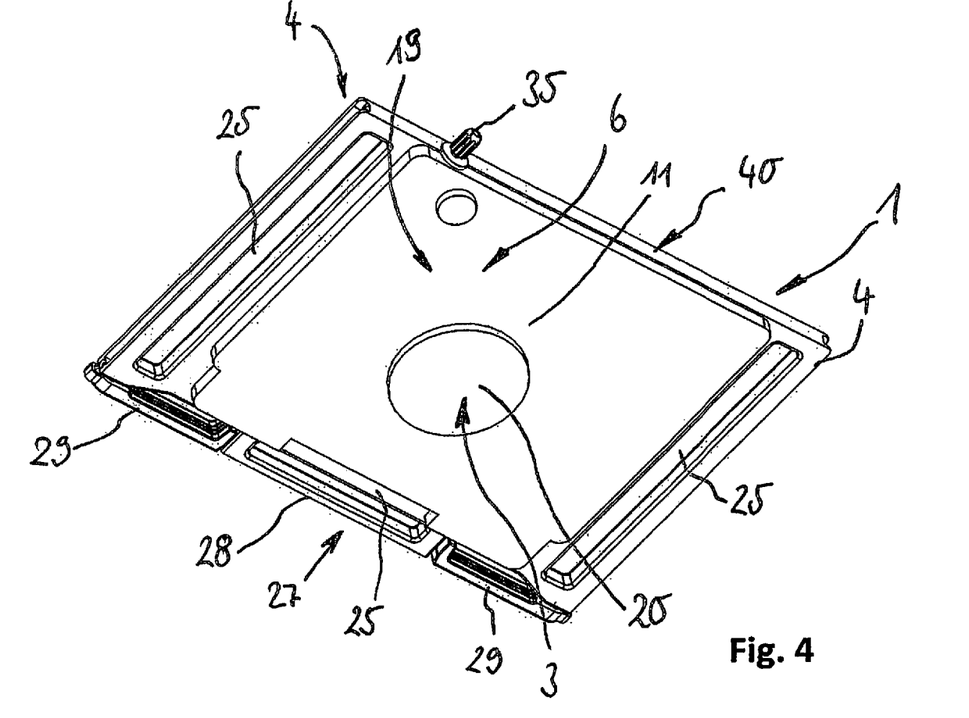
FIG. 4 shows a perspective bottom view of the insert shelf illustrated in FIGS. 1 and 2, wherein a PTO shaft of a drive apparatus of the insert shelf can be seen on the rear side of the insert shelf, this shaft being connectable to the drive motor of the incubator which is shown in FIGS. 2 and 3.

The incubator 2, which is shown in FIGS. 1 to 3, has a heatable incubation space 34. The incubator 2 shown in FIGS. 1 to 3 also has a drive motor 18 which is designed as an electric motor that can be connected to the drive apparatus 6 of the insert shelf 1, such that the movable setup area 5 of the insert shelf 1 that can be inserted into the incubator 2 in the use position, can be moved.

The preferred embodiment of the invention is to provide the drive motor 18 on the incubator 2 and not directly on the insert shelf 1 because in this way it is possible to avoid any additional heat source being disposed in the interior of the incubator 2 and/or the incubation space 34 together with the drive motor 18, which can make an accurate temperature control during an incubation process difficult.

The insert opening 26 in the incubator 2 through which on the one hand the at least one insert shelf 1 can be introduced into the incubation space 34 and through which on the other hand the incubation space 34 is accessible, can be closed// sealed by means of a cover (not shown in the figures) or a door to be able to maintain the temperature set in the incubation space 34 of the incubator 2.

As already described above, the incubator 2 has a plurality of holding elements, which are designed as holding rails 39 disposed vertically and at a distance from one another in the use position in the incubator 2 illustrated in the figures, defining individual holding stages. The holding rails 39 permit at least one insert shelf 1 and/or a plurality of insert shelves 1 to be disposed at different holding stages in the incubation space 34, disposed one above the other in the incubation space 34 at the same time.

The incubator 2 also has two centering elements, which are centering holes here, designed to fit with the two centering journals 30 on an interior wall of its incubation space 34, but not shown in the figures.

The figures do not show that the incubator 2 has two centering elements designed to correspond to the two centering elements 30 of the insert shelf 1 in each of the holding stages for the at least one shelf 1 disposed vertically and at a distance from one another in the use position.

As already mentioned above, the drive motor 18, which can be connected to the drive apparatus 6 of the at least one insert shelf 1, is disposed on the incubator 2. FIGS. 2 and 3 show that the drive motor 18 is disposed on a rear side of a housing 38 of the incubator 2, wherein a drive torque of this drive motor 18 can be transferred to at least one insert shelf 1, in particular to the movable setup area 5 and/or to the vibrating frame 11 or also to the individual magnetic stirring drives 7 by means of the belt drive 19 of the insert shelf 1.

The exemplary embodiments of the insert shelf 1 according to FIGS. 4, 5, 6, 7 as well as 10 and 11 also show that insert shelf 1 has a PTO shaft 35 on a side 40 facing away from the insert opening 26 of the incubator 2 into the incubation space 34 in the use position, and the incubator 2 has a similarly disposed coupling site 36 for the PTO shaft 35, wherein an output shaft of the drive motor 18 (not shown in the figures) can be coupled to the PTO shaft 35 of the insert shelf 1 in the coupling site 36 of the incubator 2.

The torque of the drive motor 18 can be transferred via a gear step 42 to the input disk 41 and from there to the belt drive 19 with the help of the PTO shaft 35.

In one exemplary embodiment of the incubator 2 (not shown in the figures), the incubator 2 has a plurality of holding stages, preferably a number corresponding to a number of holding stages for the at least one insert shelf 1, fitting the coupling sites 36 positioned to fit with the holding stages for a PTO shaft 35 of the at least one insert shelf 1.

In another embodiment of the incubator 2, it is also provided that the drive motor 18 can be disposed in a plurality, preferably in a number of positions on the incubator 2 and/or on its housing 38 corresponding to the number of holding stages.

In a third embodiment of the incubator 2, which is also not shown in the figures, it is provided that the incubator 2 has a plurality of drive motors 18, in particular a number of drive motors 18 corresponding to the number of holding stages and disposed on the incubator 2, so that they fit with the holding stages of the incubator 2 and each has a coupling site designed to fit with the PTO shaft 35 of the at least one insert shelf 1.

The insert shelf 1 is characterized in that it has at least one means 3 with which an incubation medium in an incubation vessel placed on the insert shelf 1 can be set in motion during an incubation treatment or during an incubation process within the incubator 2. To this end, the at least one means 3 can be operated electrically and/or preferably moved mechanically.

The invention claimed is:

1. An insert shelf (1) for an incubator (2), the insert shelf being configured to be insertable, and used in the incubator (2) in the use position to hold at least one incubation vessel and to cause motion of incubation medium disposed in the at least one incubation vessel placed on the insert shelf (1), wherein the insert shelf (1) includes a frame (4), a setup area (5), an input disk (41), an output disk (20), a belt drive (19), a vibrating frame (11), and a flange element (12), the setup area (5) defines an upper surface configured to support the at least one incubation vessel, the frame (4) defines a recess with the vibrating frame (11) being located in the recess, the flange element (12) being located within the vibrating frame (11) with the setup area (5) being fastened to the flange element (12), wherein, torque applied to the input disk (41) causes rotation thereof, resulting in rotation of the output disk (20) via the belt drive (19), the rotation of the output disk (20) imparting movement to the vibrating frame (11) to move the setup area (5) relative to the frame (4) with the frame (4) being stationary, wherein, the flange element (12) is mounted to be movable relative to the vibrating frame (11) by means of an internal pair of vibrating springs (13), and wherein the frame (4) being configured to support the insert shelf (1) in a use position in the incubator (2) with insertion of the insert shelf (1) therein.

2. The insert shelf (1) according to claim 1, wherein the vibrating frame (11) is disposed in a plane spaced from the frame (4).

3. The insert shelf (1) according to claim 1, wherein the rotation of the output disk (20) imparts eccentric movement to the vibrating frame (11).

4. The insert shelf (1) according to claim 1, wherein the insert shelf (1) has at least one convection opening (25) passing through the insert shelf (1).

5. The insert shelf (1) according to claim 1, wherein the insert shelf (1) has at least one handle (28) such that the insert shelf (1) can be inserted into the incubator (2) by means of the handle.

6. The insert shelf (1) according to claim 1, wherein the insert shelf (1) includes at least one centering journal (30).

7. The insert shelf (1) according to claim 1, wherein the insert shelf (1) has at least one of a nubby mat and an incubation vessel holder (32) for securing at least one incubation vessel on the setup area (5).

8. The insert shelf (1) according to claim 1, wherein the insert shelf (1) is provided with a non-slip coating.

9. The insert shelf (1) according to claim 1, further comprising a PTO shaft (35) for receiving torque for conveyance to the input disk (41).

10. The insert shelf (1) according to claim 1, wherein the output disk (20) includes an eccentric journal (21) being coaxially aligned with the axis of rotation of the output disk (20).

11. The insert shelf (1) according to claim 1, wherein rotation of the output disk (20) causes eccentric orbital movement of eccentric bearing (22) which imparts movement to the vibrating frame (11).

12. The insert shelf (1) according to claim 1, wherein the vibrating springs (13) are each connected to the flange element (12) and the vibrating frame (11).

13. The insert shelf (1) according to claim 1, further comprising a drive motor (18) for applying torque to the input disk (41).

14. The insert shelf (1) according to claim 13, wherein the drive motor (18) is electrically operable.

15. The insert shelf (1) according to claim 1, wherein the vibrating fame (11) is suspended by a second pair of vibrating springs.

16. The insert shelf (1) according to claim 15, wherein the second pair of vibrating springs extend from fastening heads (15) disposed on a base plate (16) located below the vibrating frame (11) opposite the setup area (5).

17. An incubator (2) having a heatable incubation space (34) and having at least one replaceable insert shelf (1) that is used in the incubation space (34) of the incubator (2) to receive at least one incubation vessel containing an incubation medium, wherein the at least one replaceable insert shelf (1) is configured as an insert shelf (1) according to claim 1.

18. The incubator (2) according to claim 17, wherein the insert shelf (1) further comprising a drive motor (18) for applying torque to the input disk (41).

19. The incubator (2) according to claim 17, wherein the insert shelf (1) further comprising a PTO shaft (35) for receiving torque for conveyance to the input disk (41).

20. The incubator (2) according to claim 19, wherein the incubator (2) has a drive motor (18) connected to the PTO shaft (35).

21. The incubator (2) according to claim 20, wherein the drive motor (18) is disposed on a housing (38) of the incubator (2).

* * * * *